(12) United States Patent
Fitchard et al.

(10) Patent No.: US 6,385,286 B1
(45) Date of Patent: May 7, 2002

(54) DELIVERY MODIFICATION SYSTEM FOR RADIATION THERAPY

(75) Inventors: Edward E. Fitchard; Gustavo H. Olivera; Paul J. Reckwerdt; Thomas R. Mackie, all of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/582,538
(22) PCT Filed: Aug. 6, 1999
(86) PCT No.: PCT/US99/17675
§ 371 Date: Jun. 28, 2000
§ 102(e) Date: Jun. 28, 2000
(87) PCT Pub. No.: WO00/07669
PCT Pub. Date: Feb. 17, 2000

Related U.S. Application Data
(60) Provisional application No. 60/095,529, filed on Aug. 6, 1998.

(51) Int. Cl.$^7$ ................................................ A61N 5/10
(52) U.S. Cl. ................................ 378/65; 378/8; 378/69
(58) Field of Search ................................. 378/65, 8, 19, 378/20, 64, 69

(56) References Cited

U.S. PATENT DOCUMENTS

| | | | |
|---|---|---|---|
| 5,418,827 A | * | 5/1995 | Deasy et al. .................. 378/65 |
| 5,673,300 A | | 9/1997 | Reckwerdt et al. ........... 378/65 |
| 5,724,400 A | * | 3/1998 | Swerdloff et al. ............. 378/65 |

FOREIGN PATENT DOCUMENTS

WO      WO 98/02091      1/1998

OTHER PUBLICATIONS

PCT International Search Report dated Dec. 2, 1999 in PCT Appln. No. PCT/US99/17675.

* cited by examiner

Primary Examiner—Drew Dunn
(74) Attorney, Agent, or Firm—Quarles & Brady LLP (57) ABSTRACT

Radiotherapy controlling, treatment sinograms may be directly modified to correct for real time motion of patients or portions of patients resulting from physiological or other activity. Precalculated partial sinograms representing treatments of portions of a patient may be assembled to obtain a treatment sinogram for the entire patient without delay from conventional planning software. The partial sinograms are modified as representations of their corresponding portions and manipulated to conform to the particular dimensions of an actual patient. This constructed sinogram may be used directly or as a starting point for iterative optimization.

20 Claims, 5 Drawing Sheets

DELIVERY MODIFICATION SYSTEM FOR RADIATION THERAPY

CROSS-REFERENCE TO RELATED APPLICATIONS

This application is a 371 of PCT/US99/17675, filed Aug. 6, 1999, which claims benefit of provisional application No. 60/095,529, filed Aug. 6, 1998.

STATEMENT REGARDING FEDERALLY SPONSORED RESEARCH OF DEVELOPMENT

This invention was made with United States government support awarded by the following agencies:
NIH Grant No. CA48902
The United States has certain rights in this invention.

FIELD OF THE INVENTION

This invention relates generally to radiation therapy equipment for the treatment of tumors or the like and specifically to a computerized method for rapidly correcting a radiation treatment plan to account for motion or change in shape of treatment areas.

BACKGROUND OF THE INVENTION

Medical equipment for radiation therapy treats tumorous tissues with high energy radiation. Such radiation may be x-ray radiation or accelerated electrons, protons, neutrons or heavy ions. The amount of radiation and its placement must be accurately controlled to ensure both that the tumor receives sufficient radiation to be destroyed and that the damage to the surrounding non-tumorous tissue is minimized.

One highly accurate method of controlling the dose to a patient employs a radiation source that produces many individual rays whose intensity and/or energy may be independently controlled. This may be done by a series of shutters each controlling one ray or by a single modulated ray moved across the patient. The origin of the rays orbits the patient within a plane of the rays to illuminate a slice of the patient, when the orbit is planar, or several slices of the patient, when the orbit is helical. By properly selecting the ray intensities and/or energies at different angles, complex regions within the slice may be accurately irradiated. A mapping of the modulation of each beam as a function of angle forms a "treatment sinogram".

U.S. Pat. No. 5,317,616 issued May 31, 1994 assigned to the same assignee as the present application and hereby incorporated by reference describes the construction of one such machine and a method of calculating the necessary beam intensities and/or energies as a function of angle.

In order to take advantage of the improved accuracy in dose placement offered by such radiation therapy systems, the radiation treatment plan may be based on a computed tomography (CT) image of the patient. As is known in the art, a CT image is produced by a mathematical reconstruction of many projection images obtained at different angles about the patient. In a typical fan beam CT acquisition, the origin of the fan beam orbits the patient within a plane of the fan to illuminate a slice of the patient, while the attenuation of each ray of the fan beam is measured as a function of that angle to obtain projections. The geometry of the CT acquisition is thus very similar to the geometry of the radiation therapy.

Each CT projection forms a one-dimensional line image indicating the attenuation of the fan beam by a "slice" of the patient. Together these line images at each angle form an "attenuation sinogram" which may be reconstructed using well known algorithms such as filtered back projection into two dimensional tomographic images of the slice. The sinographic data, which by itself is unintelligible, is normally no longer used or accessed by the user.

Using the CT image, the radiologist views the tumorous area and determines the beam angles and intensities and/or energies (identified with respect to the tumor image) which will be used to treat the tumor. In an automated system, a computer program selects the beam angle and intensities and/or energies after the physician creates a dose map identifying the tumorous region and upper and lower dose limits for regions of the treatment.

Preparing a treatment plan based on the dose map is a time consuming operation even on current high speed computers. Accordingly, the CT image of the patient is acquired before the time of radiation treatment. As a result, the patient will typically not be in the same position during the radiation treatment as the patient was during the CT imaging. The problem of properly aligning the patient is compounded when the treatment occurs in a number of different sessions over time.

U.S. Pat. No. 5,673,300 assigned to the same assignee as the present invention describes a method of determining patient movement by obtaining a second CT image immediately prior to radiation therapy and comparing the sinogram of that CT image to the sinogram of the original CT image used for radiation treatment planning. This comparison yields an indication of patient movement which may be applied directly to the treatment sinogram used to control the radiation therapy machine. This invention, by recognizing the close analogy between the attenuation sinograms of the CT image and of the treatment sinograms of radiation therapy treatment, greatly simplified detecting and correcting mis-registrations of the patient to the treatment sinogram.

BRIEF SUMMARY OF THE INVENTION

The present inventors have recognized that the above technique of directly modifying the treatment sinogram, by bypassing the time-consuming translation of dose map to treatment sinogram, makes possible real-time correction for patient motion. Such a correction may deduce real-time motion from a concurrent tomographic scan or from well known transducers used for measuring physiological motion. An improved method for correcting "fan beam" sinograms facilitates this use of the sinogram directly. The inventors have also recognized that the ability to manipulate sinograms to accommodate motion in the underlying structure, allows for a novel method of generating a treatment sinogram by combining precalculated partial sinograms representing treatments of standard elements of the patient. These standard elements may be moved to match a particular patient's anatomy and the partial sinograms modified according to the techniques described above. The partial sinograms are then combined and used directly or as a starting base for iterative treatment planning software.

Specifically, then, the present invention provides a method of operating a radiation therapy machine providing a radiation beam of individually intensity and/or energy modulated radiation rays separated along a radiation beam axis, the radiation beam axis positionable at a range of angles about a patient. A treatment sinogram is received providing intensities and/or energies of different rays for a given angle of the radiation beam, in a row, and intensities and/or energies of a given ray for different angles of the beam axis, in a column, for a patient at a first position. During radiation treatment, data indicating patient movement from the first position to a second position is also received and for each given beam axis angle of the treatment sinogram, the corresponding row of treatment sinogram is altered according to the indicated movement.

Thus it is one object of the invention to make possible real-time correction of patient motion to correct not only patient positioning errors but physiological motions such as caused by respiration and cardiac motion. Direct operation on the treatment sinogram renders such real-time control possible.

The movement may be detected by comparing a planning tomographic image of the patient contemporaneous with the preparation of the treatment sinogram to a monitoring tomographic image of the patient taken during radiation therapy. Alternatively, the patient movement may be determined by a model receiving as an input a physiological signal such as respiration or heart beat or external fiducial marks may be measured.

Thus it is another object of the invention to provide a method of detecting patient motion on a real-time basis in a radiation therapy setting.

The modification of the treatment sinogram may shift corresponding rows of treatment sinogram according to a component of patient motion perpendicular to the given beam axis.

Thus it is another object of the invention to provide an extremely simple operation on the treatment sinogram such as may be performed in real-time.

The modification of the treatment sinogram may scale corresponding rows of treatment sinogram according to a component of patient motion parallel to the given beam axis.

Thus it is another object of the invention to provide a more sophisticated modification of the treatment sinogram addressing the geometry of the highly efficient fan beam radiation therapy machine.

The present invention also contemplates the preparation of a library of partial sinograms, each partial sinogram providing intensities and/or energies of different rays at given angles of the radiation beam axis, in sinogram rows, and intensity and/or energy of given rays for different angles of the beam axis, in sinogram columns, for a patient element in first modes. Sets of representations of patient elements may be arranged in combinations at second modes so as to model a given patient requiring radiation treatment. Changes in the patient elements between the first and second modes may be captured in alteration data. This alteration data may be used to modify the partial sinograms of each of the patient elements according to the alteration data and the partial sinograms may be combined to produce a treatment sinogram of the patient.

Thus it is another object of the invention to make use of the ability to directly modify treatment sinograms to prepare template sinograms that may be simply combined to produce a treatment sinogram without the need for extensive treatment planning operations. The alteration data may indicate either change in location or dimension of the patient elements, the latter which may be simple geometric shapes or may model specific organs.

Thus it is another object of the invention to provide in a finite library of patient elements sufficient to permit assembly of an approximate treatment sinogram.

The treatment sinogram thus constructed may be further optimized to better conform with the dose map.

Thus it is another object of the invention to provide an advanced starting point for dose optimization such as may reduce the number of iterations and thus the time required to prepare the treatment sinogram.

The foregoing and other objects and advantages of the invention will appear from the following description. In the description, reference is made to the accompanying drawings which form a part hereof and in which there is shown by way of illustration a preferred embodiment of the invention. Such embodiment does not necessary represent the full scope of the invention, however, and reference must be made to the claims herein for interpreting the scope of the invention.

DETAILED DESCRIPTION OF THE INVENTION

The Radiotherapy Machine

Figure 1:
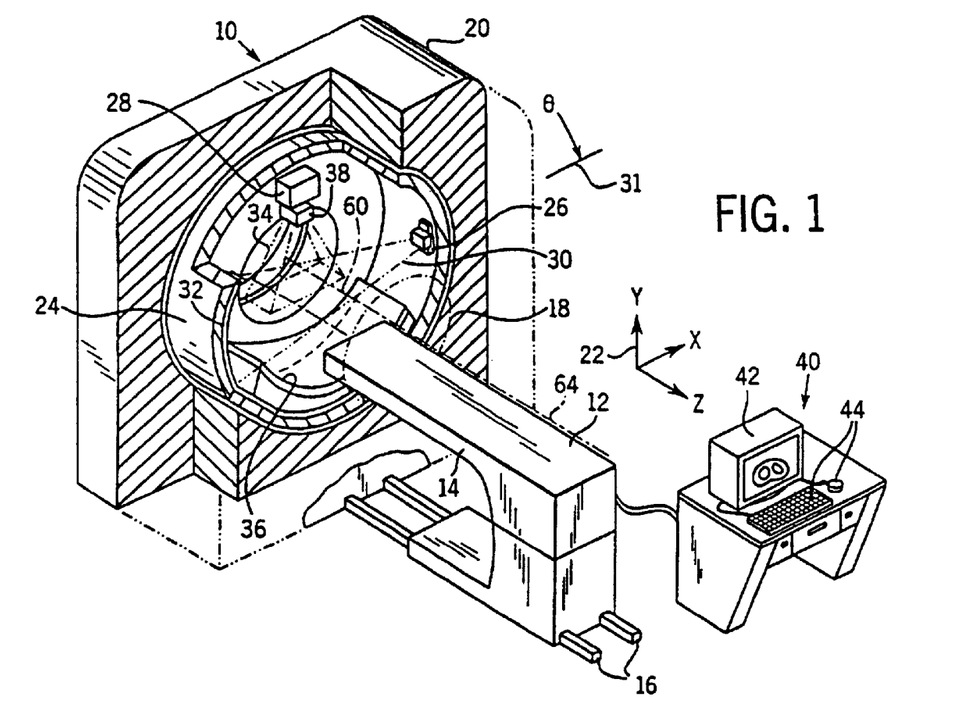
FIG. 1 is a perspective, cut-away view of a radiation therapy system providing for the acquisition of radiographic projections and for the generation of high energy radiation therapy beams and showing a patient table for supporting a patient thereon.

Referring now to FIG. 1, a radiation therapy machine 10, suitable for use with the present invention, includes a radiotranslucent table 12 having a cantilevered top 14. The table top 14 is received within a bore 18 of an annular housing 20 of the radiation therapy machine 10 with movement of the table 12 along tracks 16 extending along a z-axis of a Cartesian coordinate system 22.

Table 12 also includes an internal track assembly and elevator (not shown) to allow adjustment of the top 14 in a lateral horizontal position (indicated by the x-axis of the coordinate system 22) and vertically (indicated by the y-axis of the coordinate system 22). Motion in the x and y directions are limited by the diameter of the bore 18.

A rotating gantry 24, coaxial with the bore 18 and positioned within the housing 20, supports an x-ray source 26 and a high energy radiation source 28 on its inner surface. The x-ray source 26 may be a conventional rotating anode x-ray tube, while the radiation source 28 may be any source of treatment radiation including one producing x-rays, accelerated electrons, protons or heavy ions such as are understood in the art. The x-ray source 26 and a radiation source 28 rotate with the gantry 24 about a center of rotation 64 near the top of patient table 12 when the table top 14 is positioned within the bore 18.

The x-ray source 26 is collimated to produce a fan beam 30 lying generally within the x-y plane and crossing the bore 18 and thus the table top 14 when table top 14 is positioned within the bore 18. The fan beam 30 diverges about a central axis 31 whose angle is controlled by the position of the gantry 24. The axis 31 will henceforth be termed the projection axis.

After exiting the table top 14, the fan beam 30 is received by a linear array detector 32 positioned diametrically across from the radiation source 28. Thus, the rotating gantry 24 permits fan beam radiographic projections of a patient on the table top 14 to be acquired at a variety of angles θ about the patient.

The radiation source 28 is mounted so as to project a fan beam of high energy radiation 34, similar to the fan beam 30, but crossing fan beam 30 at right angles so as to be received on the other side of the gantry 24 by radiation detector and stop 36. In an alternative embodiment, the stop is replaced by a detector to provide an alternative to the detector 32 for deducing motion of the patient. The fan beam of high energy radiation 34 diverges about a radiation axis centered within the beam and perpendicular to the projection axis 31.

The radiation source 28 has a collimator 38 mounted in front of it to divide the beam of high energy radiation 34 into multiple adjacent rays whose energy and/or fluence may be individually controlled. As used herein, control of the energy and/or fluence of the rays should be understood to include not only the energy of individual x-ray photons (or particles in the case of radiation therapy using electrons, protons or heavy ions) but alternatively or in addition the total number of photons or particles such as is a function of fluence, fluence rate and exposure time. In the case of radiotherapy using particles, the energy of the particles, fluence and fluence rate may be controlled using sinograms which may be modified by the present invention as will be apparent from the following description.

A collimator suitable for fluence control type is described in U.S. Pat. No. 5,317,616 assigned to the assignee of the present case and hereby incorporated by reference, a simple modification of this collimator using wedge filters may be used for particle energy control. Alternatively, a scanning single beam system may be used or other system providing a set of individually modulated rays. The location of the radiation source 28 and x-ray source 26 are precisely characterized so that images obtained from the radiation source 28 may be used to aim the radiation source 28.

A computer 40 having a display screen 42 and user entry mouse and keyboard 44 well known in the art is connected to the radiation therapy machine 10 to control motion of the table 12 and to coordinate operation of the gantry 24 together with the radiation source 28 and x-ray source 26 and to collect data from the linear array detector 32 during a scan of the patient according to methods well known in the art.

CT and Radiotherapy Treatment Sinograms

Figure 2:
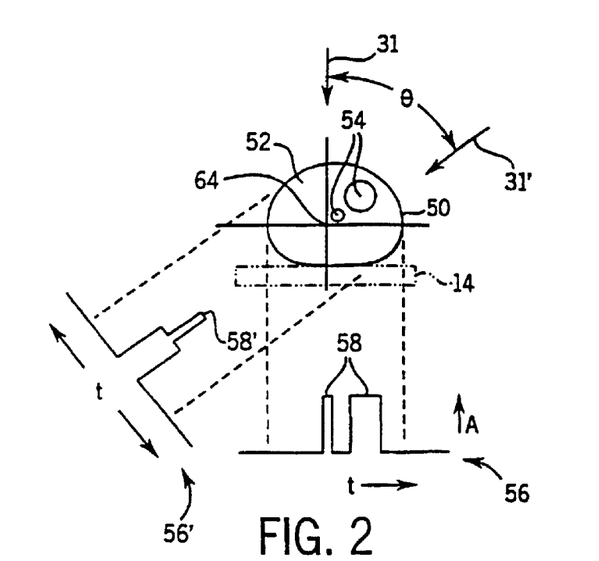
FIG. 2 is a simplified view of a slice of an object, such as a patient, showing line projections of the object taken at two angles θ, with attenuations A along dimension t indicated in the vertical axis of each projection.

Referring now to FIG. 2, a slice 50 of the patient taken along the x-y plane includes two zones 54 within a larger zone 52. Radiation passing along beam axis 31 through the slice 50 (at a vertical or anterior/posterior angle ("AP")) produces a projection 56 which records the attenuation of x-rays passing through to slice 50 along a single line perpendicular to the beam axis 31 (for CT) or provides a radiation treatment projection of different e energy and/or intensity of beams corresponding to the different zones 52 and 54 (for radiotherapy). In either case, the distance along this perpendicular to the projection axis is designated: t. The zones 54 may be resolved separately at the vertical angle and hence two peaks 58 (attenuation or radiation energy and/or intensity) are present in the projection 56.

Figure 3:
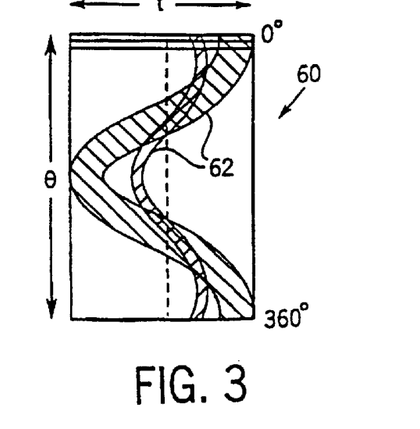
FIG. 3 is a sinogram formed of multiple line projections such as those acquired in FIG. 2, over 360 degrees of angle θ with the attenuation of the projections indicated by shading.

In contrast at a second projection along a projection axis 31' at an angle θ from vertical, the zones 54 are aligned so that the projection 56' shows a single peak 58';

Referring now to FIG. 3, projections at a different angle θ over 360 degrees, may be combined to form an sinogram 60 which is stored temporarily in computer 40 as a matrix of data. As depicted, this matrix of data is arranged with each row representing a different angle θ and each column a different distance t along the projection. For a CT attenuation sinogram, each element of the matrix is a value of attenuation. For a radiation treatment sinogram, each element of the matrix is an energy and/or fluence of a ray of the treatment beam. The values may be stored as numeric variables in the computer 40 and are shown as shaded curves 62.

The pattern of the sinogram 60 is generally that of superimposed sinusoidal curves 62 (hence the name) each curve 62 having a fundamental period in θ of 360 degrees as a result of the apparent movement of zones 54 in orbit about a center of gantry rotation 64 as projections are taken at various angles θ. Generally, zones 54 toward the axis of rotation 64 of the gantry trace smaller amplitude sine curves whereas zones 54 further from the center of rotation 64 trace greater amplitude sine curves. The phase of the sine curves depends generally on the initial position of the zones 54 with respect to the first projection at θ=0.

In a conventional CT acquisition, an attenuation sinogram may be reconstructed into a tomographic image of the slice 50. As is well understood in the art, an attenuation sinogram having t values spanning the largest cross-sectional width of an imaged slice 50 and θ values over 360 degrees is sufficient to reconstruct a tomographic image of the slice through, for example, the method of filtered back projection.

In radiation therapy, a treatment sinogram may be used to control the e energy and/or fluence of adjacent rays of a fan beam of high energy radiation 34 transmitted through the patient. For example, if the zones 54 of FIG. 2 were tumors, a radiation treatment plan might well conform generally to curves 62 which would produce beams of high intensity radiation that would intersect at the zones 54 at a variety of different angles θ to produce a high cumulative dose at the zones 54 but low elsewhere.

Referring again to FIG. 1, it follows that the tomographic image produced from the sinogram 60 may be employed to establish a radiation treatment plan precisely related to that tomographic image. U.S. patent application Ser. No. 08/477,055 filed Jun. 7, 1995, hereby incorporated by reference, describes generally an interactive method for generating a treatment plan in the form of a sinogram 60 based on a tomographic image.

Figures 4, 5, 6:
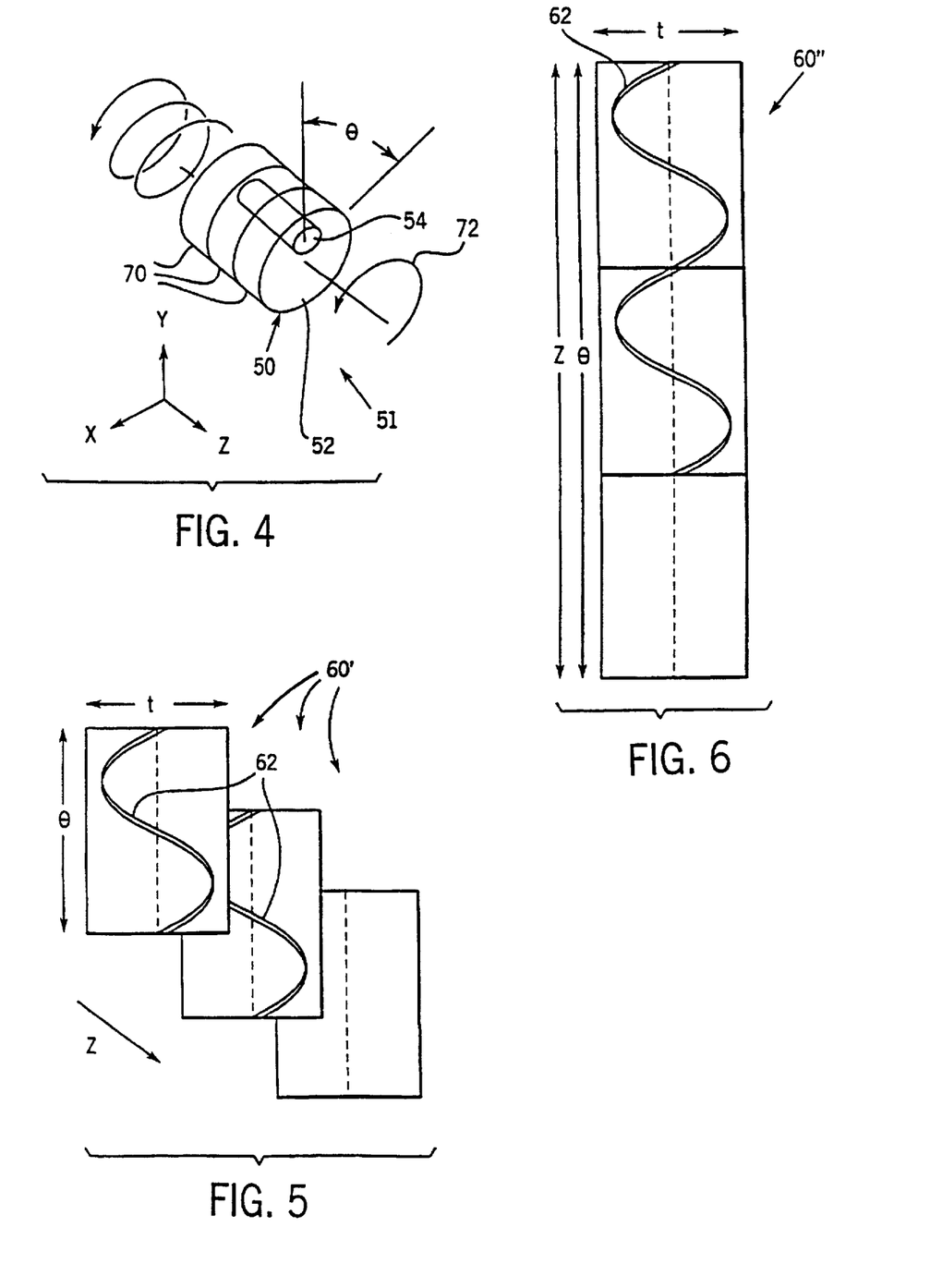
FIG. 4 is a perspective view of a simplified object that may be scanned showing a helical and slice-by-slice scanning path.
FIG. 5 is a set of sinograms of the object of FIG. 4 such as may be obtained in a slice-by-slice scanning.
FIG. 6 is a sinogram of the object of FIG. 4 such as may be obtained in a helical scan.

Referring now to FIG. 4, in a "slice-by-slice" tomographic acquisition or in a slice-by-slice radiation treatment, the imaged object 51 is divided into a plurality of slices 70 separated along the z-axis and the acquisition of projections or the radiation treatment is obtained with the beam axis 31 constrained to a single plane as it rotates about the imaged object 51 indicated generally by arrow 72. At the conclusion of 360 degrees of rotation the object is moved along the z-axis by movement of the table 12 until the next slice is aligned with the beam axis 31.

In an alternative acquisition or treatment method termed "helical scanning", the projection axis follows a helical path through the imaged object 51 in which the table 12 is incremented by a small amount in z with each change in angle θ.

In the former slice-by-slice method, a series of sinograms 60' is used (attenuation and treatment), each one identical to that described with respect to FIG. 3 and typically encompassing 360 degrees of gantry motion. Different slices 70 produce different ones of a sequence of sinogram 60' each of which has a different but constant z value.

In contrast, the helical acquisition produces a sinogram 60" in which each row of the sinogram 60" represents a different increment in both θ and in Z.

In the example shown in FIG. 4, a zone 54 extends only through the first two slices 70. Hence, in FIG. 5, only the first two sinograms 60' show sine curves 62 related to the zone 54. Likewise, in the helically acquired sinogram 60" of FIG. 6 only the first 720 degrees of the sinogram 60" show a sign curve 62.

The Treatment Planning Process

Figure 7:
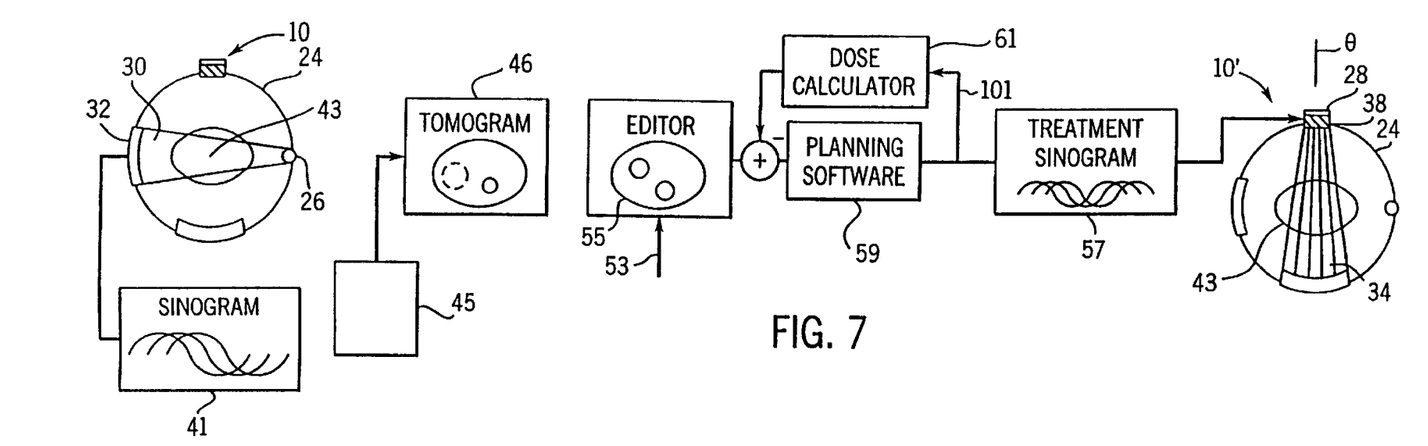
FIG. 7 is combination block diagram and flow chart showing the steps of preparing a treatment sinogram used for controlling a radiation therapy machine, from a computed tomography scan taken on the same or a different machine.

Referring now to FIG. 7, the radiation therapy machine 10 or an independent CT machine (not shown) may be used to acquire tomographic data in the form of an attenuation sinogram 41 of a patient 43. As described above, the attenuation sinogram 41 generally provides rows (here depicted vertically) comprising a set of attenuation measurements A(t) received by the detector 32 at different rays at a given projection angle θ and columns (here depicted horizontally) representing the same data for different projection angles θ.

The attenuation sinogram 41 is received by a tomographic reconstructor 45 such as one using well known filtered backprojection algorithms to provide a planning tomographic image 46 depicting a slice of the patient 43. This and the following steps may be performed on computer 40.

The planning tomographic image 46 may be provided to a dose map editor 48 where it provides a background on which a dose map 55 is prepared by a physician. The dose map 55 depicts the desired dose in regions within the slice of the patient 43.

In the preferred embodiment, the dose map 55 is prepared interactively with editing commands 53 from a keyboard or cursor control device being received by the dose map editor 48.

The dose map 55 is used to prepare a treatment sinogram 57 describing energy and/or fluence of plurality of radiation beams from the radiation source 28 at different beam angles θ that will produce the desired dose of the dose map 55. The treatment sinogram 57 is generally arranged with rows (here depicted vertically) providing values of a function I(t) indicating beam energy and/or fluence for different rays t within a beam and columns (here depicted horizontally) providing values of a function I(θ) indicating beam energy and/or fluence for different beam angles θ.

Generally the process of converting the dose map 55 to the treatment sinogram is performed as an iterative optimization by planning software 59. The planning software 59 produces a trial sinogram 101 which is provided to a dose calculator 61, the latter which determines the dose that would be produced by the trial sinogram and comparing it to the desired dose as indicated by comparison node 102. The planning software 59 receiving an indication of the deviation between the dose provided by the trial sinogram 101 and the dose map 55 then modifies the beam energy and/or fluence of the trial sinogram 101 according to that deviation and the process is repeated until a treatment sinogram 57 is obtained. The treatment sinogram 57 is then provided to control the collimator 38 for treatment of the patient 43.

Because of the time required to perform the actual radiation treatment using the treatment sinogram 57, patient movement caused by respiration and other sources is inevitable. This movement can be detected, but the time required to change the dose map 55 to reflect the movement and recalculate the treatment sinogram 57 is too great to practically account for short term patient movements. The present invention has recognized that with high speed computers, the pretreatment patient position correction technique described generally in U.S. Pat. No. 5,673,300 assigned to the same assignee as the present invention, can be used to also correct for motion during the treatment process itself.

Figure 8A:
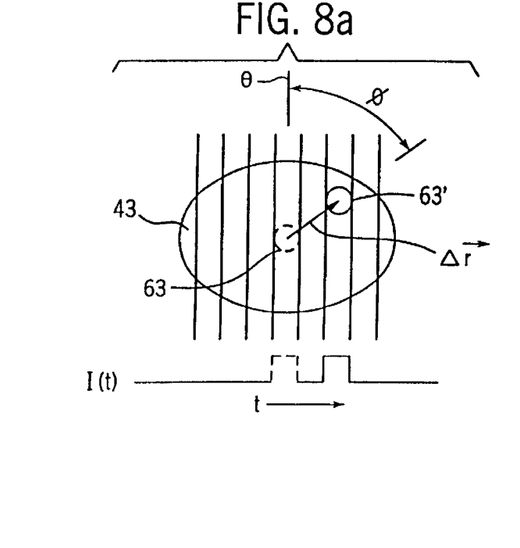
FIGS. 8a and 8b are figures similar to FIG. 2 showing the effect of movement of a structure in a parallel beam and fan beam system, respectively.
Figure 8B:
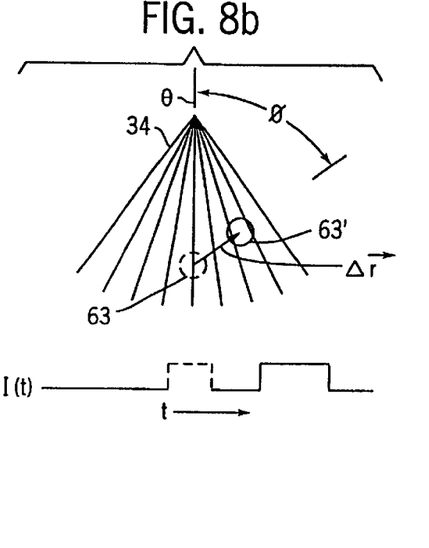

As depicted in FIG. 8a, relative motion of the patient 43 or a portion of the patient 43 by an amount $\Delta \bar{r}$ from a first position 63 to a second position 63' will require a shifting of the rows of the sinogram modifying I(t) to be I(t+$\Delta \bar{r}_\perp$) where $\Delta \bar{r}_\perp$ is an amount proportional to $\Delta \bar{r}$ times φ being the difference between the beam angle θ for that row of the sinogram and the angle of $\Delta \bar{r}$. This correction alone is sufficient for parallel ray systems in which each of the rays of high energy radiation 34 are parallel (shown in FIG. 8a), but is only part of the correction desired for a fan ray system where each of the rays of the high energy radiation 34 diverge about the beam axis from a common origin as depicted in FIG. 8b.

The present inventors have realized that the divergence of the rays in a fan beam system cause a magnification effect which ideally should be compensated. Referring then to FIG. 8b, an arbitrary motion of an object from position 63 to position 63' by $\Delta \bar{r}$ provides not only a shifting of the sinogram rows I(t) but can provide a magnification of that function. Thus the object at position 63' moving closer to the origin of the fan beam as well as across the origin of the fan beam causes a shifting of the function I(t+α) and a scaling of the function I(βt) reflecting the relative magnification effects caused by moving toward and away from the origin of the fan beam of high energy radiation 34. The amounts α and β depend on the particular dimensions of the radiation therapy machine 10 and will generally be functions of the amount of motion and the origin of the motion and may be determined by well understood geometric techniques. Generally the scaling and shifting need not be linear functions and need not be uniform over the patient.

Correction of the treatment sinogram, as described above, may be provided in a number of ways. In a first embodiment shown in FIG. 9, the rows and columns of the treatment sinogram are rebinned to reflect a sinogram providing an identical radiation pattern but on a machine having parallel rays. This rebinning process is a geometric transformation well understood in the computed tomography art and may be calculated on-the-fly using mathematical formulas or by precalculated to produce a table mapping elements of the fan beam treatment sinogram 57 to corresponding elements of a parallel ray sinogram. Generally, an interpolation step will be required so that the elements map to the integer ray and beam angle values of the sinogram. This rebinning is indicated by process block 81.

Figure 9:
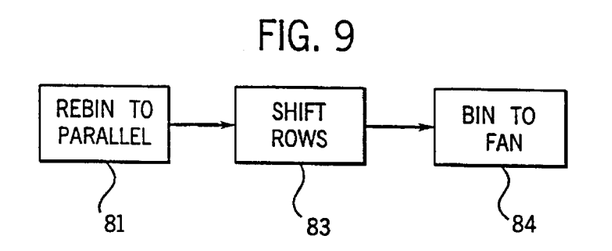
FIG. 9 is a flow chart showing the steps of a first method of correcting for motion within a fan beam involving rebinning the fan sinogram to a parallel configuration.

Next at process block 83 for each beam angle, the component of the motion perpendicular to the beam angle is determined and used to shift the particular row of the sinogram in direct proportion to that component. Motion parallel to the beam angle may be disregarded as a result of the parallel ray geometry.

At process block 84, the resultant shifted parallel ray sinogram may be rebinned to a divergent ray sinogram using the inverse process described with process block 81. The resultant sinogram will have been corrected both for parallel and perpendicular motion of the patient.

Figure 10:
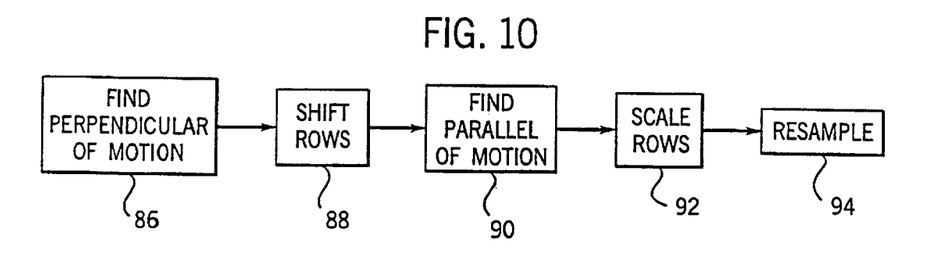
FIG. 10 is a flow chart similar to that of FIG. 9 showing a second method of correcting for motion within a fan beam involving direct mathematical manipulation by scaling and shifting of the treatment sinogram without rebinning to parallel beam configuration.

Alternatively as depicted by FIG. 10, for each row of the treatment sinogram related to a particular beam angle, a perpendicular component $\Delta \vec{r}_\perp$ of motion $\Delta \vec{r}$ may be determined as indicated by process block 86. Then at process block 88, the rows may be shifted proportionally to this component and the magnification caused by the diverging rays of the fan beam. Next at process block 90, the parallel component of the motion $\Delta \vec{r}_\parallel$ with respect to a beam axis at θ may be determined and at process block 92, the rows may be scaled appropriately. Finally, at process block 94, the scaled and shifted rows may be resampled to fit within the integer values allowed in the treatment sinogram 57.

The perpendicular value of the motion $\Delta \vec{r}_\perp$ and the parallel component of the motion $\Delta \vec{r}_\parallel$ may be deduced for any arbitrary displacement of $\Delta x$ and $\Delta y$ within a fixed x-y coordinate system lying in the plane of the fan beam according to the following formula:

$$\begin{pmatrix} \cos\phi & -\sin\phi \\ \sin\phi & \cos\phi \end{pmatrix} \begin{pmatrix} \Delta x \\ \Delta y \end{pmatrix} = \begin{pmatrix} \Delta \vec{r}_\perp \\ \Delta \vec{r}_\parallel \end{pmatrix} \quad (1)$$

For a fan beam system using a multileaved collimator, generally the corrected sinogram I(βt+α) will have discontinuities that do not lie on the separation between the leaves of the collimator 38 which define the rays. For this reason, the sinogram will have to be resampled to fit within the confines of the treatment sinogram 57. Standard methods of interpolation can be used for this resampling. The inventors recognize that there are additional errors in this approach including the failure to account for scatter but it is believed that these errors are small or can be corrected for.

Figure 12:
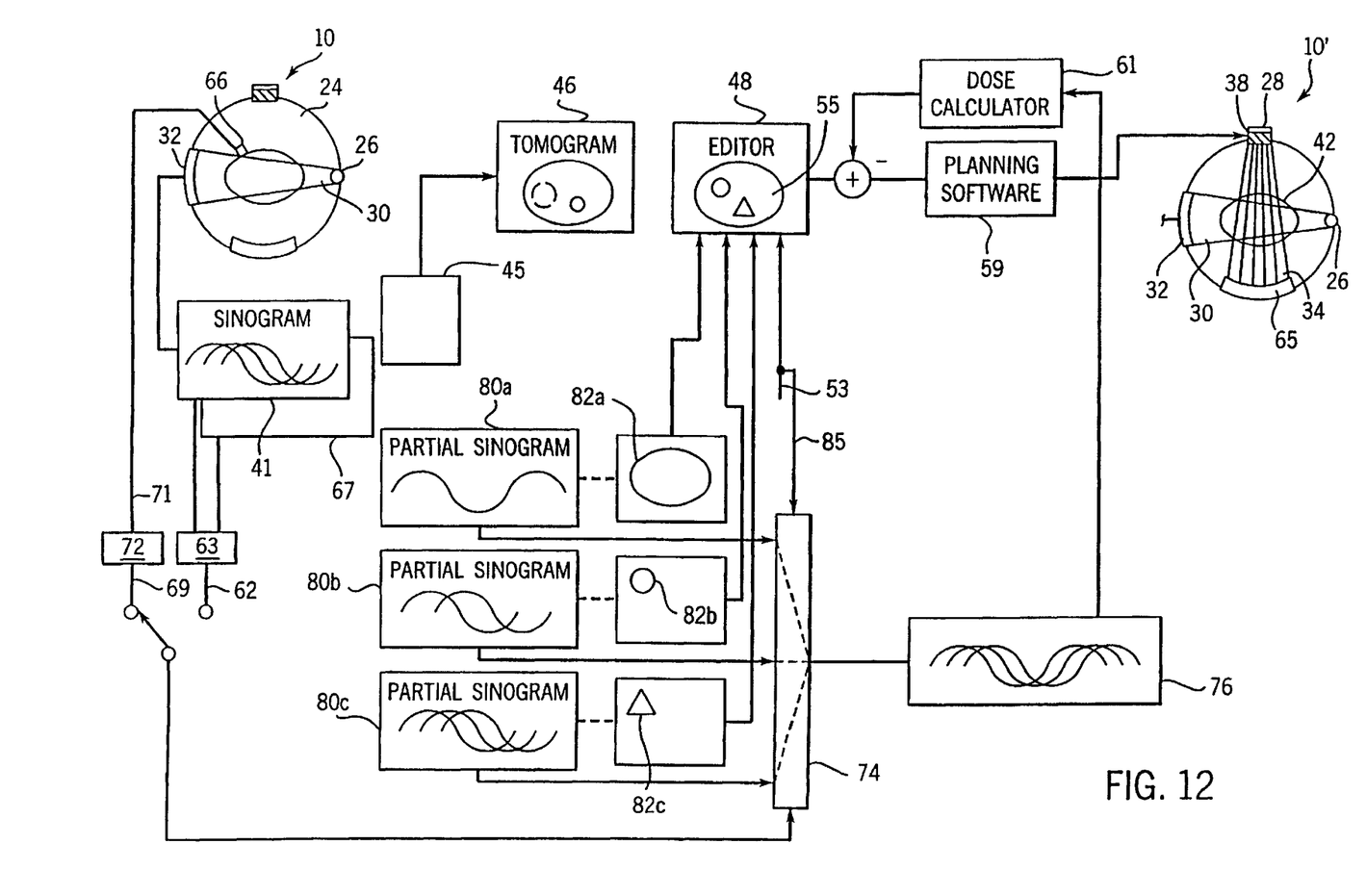
FIG. 12 is a figure similar to that of FIG. 7 showing elements of the real-time motion correction employed by the present invention and the construction of a treatment sinogram from precalculated partial sinograms.

Referring now to FIG. 12, the above described treatment sinogram modification technique or the more simple treatment sinogram modification described in predecessor parent U.S. Pat. No. 5,673,300 may be used to provide for real-time motion correction. During the treatment of the patient 43 with radiation therapy machine 10', a regular tomographic projection signal may be obtained using detector 32 or a megavoltage tomographic projection signal may be obtained by using a megavoltage detector 65. The images thus obtained may be used to provide a real-time imaging sinogram 67 which may be compared to the planning attenuation sinogram 41 as indicated by comparison block 83 according to the techniques described in the above mentioned patent to provide a motion signal 69.

Generally the comparison between the two attenuation sinograms 41 and 67 correlates rows of the sinograms at particular beam angles to determine patient motion in one or more orthogonal axes. More generally, this technique may be expanded to completely define the motion of the patient 43 in six parameters of x, y and z and roll, yaw and pitch.

Alternatively, a patient motion sensor 66 may be used to provide a physiological signal from the patient indicating motion. The sensor 66 in its simplest case may be a pressure cuff to detect chest wall expansion commensurate with breathing or may simply detect an electronic signal such as an ECG signal. The thus detected signal 71 may be provided to a mathematical model 73 relating the cycle of the signal to internal changes in the patient either through the use of a simple mathematical modeling of the patient, for example, breathing as an expansion of a generally oval chest wall, or by keying different phases of the cycle of the signal to measured tomographic images of the patient or of a standard patient that would indicate changes in location or aspect of internal structures of the patient 43. The patient motion sensor may alternatively be optical, using external fiducial marks optically detected by lasers or the like, or may employ signals from other known imaging systems such as magnetic resonance imaging (MRI) or may be provided by positioning fixtures attached to the patient employing well know location/orientation determining technologies such as those using radio or light transmitters and receivers as are known for virtual reality headsets and the like.

These signals 69 from either source may be provided to a sinogram manipulation program 74 implemented as software in a high speed computer processor performing the transformations described above, the inputs describing the $\overline{\Delta r}$ $\overline{\Delta r}$ value and absolute coordinate information. The sinogram manipulation program 74 thus receives a sinogram as prepared above as described in FIG. 7 to produce a modified treatment sinogram 76 which may be provided to the collimator 38 on a real-time basis so as to modify the actual radiation treatment on a real-time basis.

The ability to modify the treatment sinogram 57 through simple mathematical operations such as shifting and scaling provides the ability to make the rapid corrections required of real-time. Further in the case where a model 73 is used, modifications may be anticipated and calculated in advance, and/or multiple modified treatment sinograms 76 may be precalculated and simply switched into communication with the collimator 38 as required.

Figure 11:
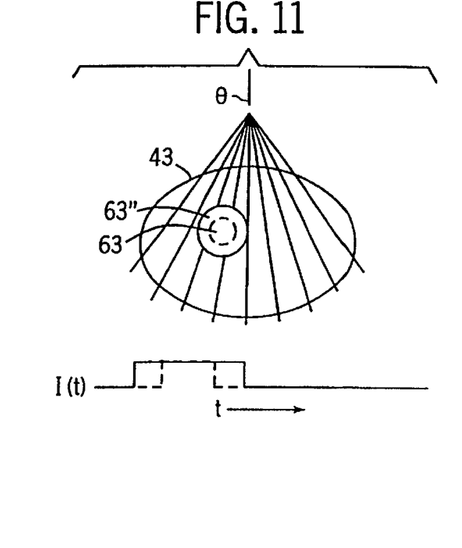
FIG. 11 is a figure similar to that of FIGS. 2, 8a and 8b showing the effect of inplace expansion of an object in contrast to translative movement of FIGS. 8a and 8b.

Referring now again to FIG. 11, the correction process applied to the sinogram need not only deal with displacement of objects, either within the patient or including the entire patient, but may accommodate general dimensional changes of objects within the patient to a limited degree. For example, object in mode 63 may inflate to become object in mode 63" to the predictable effect of expanding by scaling the sinogram function I(t) necessary to continue to treat that structure. Unlike the expansion of FIG. 4, however, a similar expansion in this case is found in all beam angles. Thus complex organ dimensional changes may be accommodated through this technique without the need for recalculation of the dose map 55.

This ability to modify the treatment sinogram 57 to change the location and dimensions of the structures they treat, allows a novel method of rapidly constructing treatment sinograms which avoids the need for conventional planning software or limits the need for such software's iterations.

Referring again to FIG. 12, such a system prepares a series of partial sinograms 80(a) through 80(c) each corresponding to a predetermined patient element 82(a) through 82(c) and providing a standard treatment for those elements. These partial sinograms 80(a) through 80(c) may be prepared using conventional planning software and optimized over the course of an arbitrarily long period of time and then stored for later use in an electronically accessible library together with representations of patient elements 82(a) through 82(c) indicating an area, possibly an expected material, and a desired treatment dose.

During the planning process, the dose map editor 48 receives representations corresponding to the treatment zones and doses of patient elements 82(a) through 82(c) and allows them to be manipulated with respect to the planning tomographic image 46 both by translation with respect to the planning tomographic image 46 and by expansion and contraction. These manipulation commands are received as editing commands 53 and are also provided via line 85 to the sinogram manipulation program 74.

As the patient elements 82(a) through 82(c) are manipulated, the sinogram manipulation program 74, modifies the partial sinograms 80(a) through 80(c) as has been described above to conform to the new spatial locations and dimensions of their associated patient elements 82. The sinograms 80(a) through 80(c) for the selected patient elements 82(a) through 82(c) used in the creation of a dose map 55 may then be summed or otherwise combined to produce the treatment sinogram 76. The combination operates on element pairs of corresponding rows and columns.

Thus a physician wishing to treat a tumorous organ might select a patient element 82(a) representing a preplanned treatment for that organ based on some average person and combine it with a second patient element 82(a) representing a nearby sensitive structure where radiation is to be avoided. These two portions may be placed upon a representation of the patient's torso also modeled by a portion as aligned against a tomographic image of an actual patient.

The resulting treatment sinogram 76 may be provided directly to the collimator 38 or may be used as a starting point for further optimizations using the iteration of the dose calculator 61 and the planning software 59 as has been described before.

The patient elements may thus represent either standard organs or standard geometric shapes of predetermined density and a desired dose. To the extent that many patient's treatments will be similar, except for minor anatomical dimensional variations, such a system allows the physician to use proven radiation therapy techniques across patients.

The technique of preparing a treatment sinogram from partial sinograms 80 may be further augmented by the motion detection provided by signals 69 to the extent that motion identified to a particular organ may be identified to a single, partial sinogram 80 and thus distinguishable from the other components of the treatment sinogram 57 allowing adjustment of that organ in isolation.

The above description has been that of a preferred embodiment of the present invention, and it will occur to those that practice the art that many modifications may be made without departing from the spirit and scope of the invention. In order to apprise the public of the various embodiments that may fall within the scope of the invention, the following claims are made.

We claim:

1. A method of operating a radiation therapy machine providing a radiation beam of individually energy and/or fluence modulated radiation rays directed along a radiation beam axis, the radiation beam axis positionable at a range of angles about a patient, the method comprising the steps of:
   (a) accepting a ray treatment sinogram of rows and columns providing energy and/or fluence of different rays for a given angle of the radiation beam axis, in rows, and energy and/or fluence of a given ray for different angles of the beam axis, in columns, for a patient at a first position;
   (b) developing patient movement data indicating patient motion from the first position to a second position;
   (c) for each given beam axis angle of the ray treatment sinogram shifting the corresponding row of the treatment sinogram according to a component of the patient motion perpendicular to the given beam axis and scaling the corresponding row of the ray treatment sinogram according to a component of the patient motion parallel to the given beam axis;
   whereby divergence of the fan beam of treatment radiation may be accommodated.

2. The method of claim 1 wherein step (c) is performed by:
   (i) rebinning the ray treatment sinogram into a parallel ray treatment sinogram providing equivalent treatment of the patient in the first position with a virtual radiation therapy machine having individually energy and/or fluence modulated radiation rays separated but mutually parallel along a divergence axis about a radiation beam axis;
   (ii) for each given beam axis angle of the parallel ray treatment sinogram shifting the corresponding row of the treatment sinogram according to a component of the patient motion perpendicular to the given beam axis;
   (iii) reverse rebinning the parallel ray treatment sinogram as modified by step (ii) back to a ray treatment sinogram.

3. The method of claim 1 wherein step (b) develops patient movement data by comparing tomographic images of the patient in the first and second positions.

4. The method of claim 1 wherein step (b) develops patient movement data by a patient movement model receiving as an input a physiological signal selected from the group consisting of: a respiration signal and a heartbeat signal.

5. The method of claim 1 wherein the radiation therapy machine provides the individually energy and/or fluence modulated radiation rays by means of a multi-leaf collimator having fixed leaf separation and wherein step (c) further includes the step of resampling the modified rows of the diverging ray treatment sinogram to conform with the leaf reparation of the multi-leaf collimator.

6. The method of claim 1 wherein the patient motion is non-uniform such as caused by a change in shape of internal structure to the patient and wherein at step (c) the component of the patient motion perpendicular to the given beam axis and the resultant shifting are a function of position perpendicular to the given beam axis and the component of the patient motion parallel to the given beam axis and the resulting scaling are functions of position parallel to the given beam axis;
   whereby expansion and contraction of internal organs may be accommodated.

7. A method of operating a radiation therapy machine providing a radiation beam of individually energy and/or fluence modulated radiation rays directed generally along a beam axis and spaced apart perpendicular to the beam axis, the radiation beam axis positionable at a range of angles about a patient, the method comprising the steps of:

(a) accepting a treatment sinogram of rows and columns providing energy and/or fluence of different rays for a given angle of the radiation beam axis, in rows, and energy and/or fluence of a given ray for different angles of the beam axis, in columns, for a patient at a first position;

(b) during radiation treatment using the treatment sinogram;
  (i) detecting patient movement data indicating patient motion from the first position to a second position;
  (ii) directly modifying the treatment sinogram according to the detected patient motion;

(c) continuing the radiation treatment using the treatment sinogram as modified by step (b)(ii);

whereby rapid adjustments to the treatment plan may be effected.

8. The method of claim 7 wherein step (b)(i) develops patient movement data by comparing tomographic images of the patient in the first position with tomographic images of the patient in the second position taken during radiation therapy.

9. The method of claim 1 wherein step (b)(i) develops patient movement data by a patient movement model receiving as an input a physiological signal selected from the group consisting of: a respiration signal and a heartbeat signal.

10. The method of claim 9 wherein the modification of the treatment sinogram shifts corresponding rows of the treatment sinogram according to a component of the patient motion perpendicular to the given beam axis.

11. The method of claim 10 wherein the radiation therapy machine provides the individually energy and/or fluence modulated radiation rays by means of a multi-leaf collimator having fixed leaf separation and wherein the modification of the treatment sinogram further includes the step of resampling the modified rows of the treatment sinogram to conform with the leaf separation of the multi-leaf collimator.

12. The method of claim 9 wherein the change in patient position is non-uniform such as caused by a change in shape of internal structure to the patient and wherein the rows of the treatment sinogram are modified by a shifting that is a function of the position perpendicular to the given beam axis;

whereby change of shape of internal organs may be accommodated.

13. The method of claim 7 wherein step (b)(i) develops patient movement data through a motion sensor selected from the group consisting of: a magnetic resonance imager; an optical scanner, and a location fixture attached to the patient.

14. A method of operating a radiation therapy machine providing a radiation beam of individually energy modulated radiation rays directed generally along a beam axis and spaced apart perpendicular to the beam axis, the radiation beam axis positionable at a range of angles about a patient, the method comprising the steps of:

(a) preparing a library of partial sinograms of rows and columns, providing energy and/or fluence of different rays for a given angle of the radiation beam axis, in rows, and energy and/or fluence of a given ray for different angles of the beam axis, in columns, each partial sinogram corresponding to one of a variety of patient elements in first modes;

(b) arranging combinations of a set of representations of the patient elements to second modes so as to model a given patient requiring radiation treatment;

(c) determining for each of the patient elements of the set alteration data indicating changes in the patient elements between the first and second modes;

(d) modifying the partial sinograms of each of the patient elements of the set according to the alteration data; and (e) combining the modified partial sinograms to provide a treatment sinogram of the patient.

15. The method of claim 14 wherein the alteration data indicates changes in location and dimension of the patient elements.

16. The method of claim 14 wherein in step (d) for each given beam axis angle of each partial sinogram, the corresponding row of the partial sinogram is shifted according to a component of the alteration of the patient element perpendicular to the given beam axis and the corresponding row of the partial sinogram is scaled according to a component of alteration of the patient element parallel to the given beam axis.

17. The method of claim 14 wherein prior to step (c) the arrangement of the patient elements is further modified by real-time data indicating motion of the patient.

18. The method of claim 14 wherein that patient elements are simple geometric regions.

19. The method of claim 14 wherein that patient elements are models of patient organs.

20. The method of claim 14 wherein the partial sinograms are arranged according to a dose map for the patient and including between steps (d) and (e) the step of optimizing the treatment sinogram to better conform with the dose map.

* * * * *